United States Patent [19]

McDermott et al.

[11] Patent Number: 5,928,564
[45] Date of Patent: Jul. 27, 1999

[54] LIQUID INJECTION MOLDING INHIBITORS FOR CURABLE COMPOSITIONS

[75] Inventors: Philip J. McDermott, Albany; Michael J. O'Brien, Clifton Park; Edward M. Jeram, Burnt Hills, all of N.Y.

[73] Assignee: General Electric Company, Pittsfield, Mass.

[21] Appl. No.: 08/969,157

[22] Filed: Nov. 12, 1997

Related U.S. Application Data

[62] Division of application No. 08/588,594, Jan. 18, 1996, which is a division of application No. 08/096,314, Jul. 23, 1993, Pat. No. 5,506,289.

[51] Int. Cl.⁶ .................................................. C09K 15/06
[52] U.S. Cl. ............................................................ 252/407
[58] Field of Search .............................................. 252/407

*Primary Examiner*—Kriellion S. Morgan
*Attorney, Agent, or Firm*—Kenneth S. Wheelock; Michelle Bugbee

[57] ABSTRACT

Acetylenic maleates, fumarates and related derivative compounds are new compositions of matter having the formula:

$$R_1O_2C-CH=CH-CO_2R_2$$

wherein $R_1$ may be an organic moiety containing at least two carbon atoms triply bonded one to the other as:

$$-C\equiv C-$$

and $R_2$ may be hydrogen, an organic moiety, or $R_1$; suitable for use as liquid injection molding inhibitors either singly or in combination with themselves or other liquid injection molding inhibitors when used for the process of liquid injection molding curable compositions enabling an increase in the size of articles manufactured therefrom, which new compositions of matter cure into the polymerizable or curable resins thereby creating new compositions of matter as cured resins from which said articles of manufacture are produced.

14 Claims, No Drawings

LIQUID INJECTION MOLDING INHIBITORS FOR CURABLE COMPOSITIONS

This is a divisional of application Ser. No. 08/588,594 filed on Jan. 18, 1996, which is a divisional of Ser. No. 08/096,314 filed on Jul. 23, 1993, now issued patent U.S. Pat. No. 5,506,289.

FIELD OF THE INVENTION

The present invention relates to translucent, high strength, organopolysiloxane, liquid injection molding compositions, liquid injection molding inhibitors for use with curable compositions suitable for liquid injection molding, and articles manufactured therefrom and therewith using the techniques of liquid injection molding.

BACKGROUND OF THE INVENTION

Note: In the present specification, the word resin has been used with two meanings customary in the art. The first meaning refers to a composition that is injected into a liquid injection molding apparatus and is very broad with respect to the chemical composition of its component parts. The second meaning is more specific to the chemistry of organopolysiloxanes and related silicone polymers, referring there to MQ, MDQ, MTQ, or MDTQ and similar compositions that may or may not comprise a precursor feedstock to a liquid injection molding apparatus.

Liquid injection moldable organopolysiloxane compositions are known and used. A problem with all such compositions is that the hardness, tensile strength, elongation and tear are so interdependent among themselves and also with the viscosity of the uncured liquid precursor that it is difficult to improve one property without deleterious effects on the other properties. Additionally, the kinetics and thermochemistry of the liquid injection molding process and the compositions used therewith have been such that only small lightweight articles of manufacture could be made by the techniques of liquid injection molding because of the speed with which the liquid precursor cures once it has been injected into the mold.

Liquid injection molding organopolysiloxane compositions are typically provided as two components that are mixed immediately prior to use. Both components contain alkenyl polymers, fillers, and in some cases resins. The first component contains a platinum catalyst while the second component contains a hydride cross linker and cure inhibitors. The two components are mixed immediately prior to use in the injection molding apparatus. In addition to providing a so-called formulation pot-life, the inhibitor must prevent curing of the curable composition until the mold is completely filled. Once the mold is completely filled the inhibitor must then allow for a rapid cure of the curable or polymerizable composition in order to ensure a short cycle life.

U.S. Pat. Nos. 3,884,866 and 3,957,713 describe high strength addition cured compositions suitable for low pressure liquid injection molding. These compositions comprise a first component containing a high viscosity vinyl endstopped organopolysiloxane, a low viscosity vinyl containing organopolysiloxane, filler, and platinum catalyst which is cured by mixing with a second component containing a hydrogen silicone composition. This composition has a low durometer, ca 20–35 Shore A, and, moreover it is difficult to increase the durometer or hardness without adversely affecting other properties.

U.S. Pat. No. 4,162,243 discloses compositions similar to the previously referenced compositions but they contain as the most important distinction, fumed silica that has been treated with hexamethyidisilazane and tetramethyidivinyidisilazane. The compositions of the '243 patent cure to elastomers having high hardness with good retention of other properties including strength, elongation, and tear in addition to having a low viscosity in the uncured state.

U.S. Pat. No. 4,427,801 extends the teaching of the '243 patent by incorporating a $MM^{Vi}Q$ resin in addition to the vinyl containing treated fumed silica. This produces elastomers having even a higher hardness and tear strength but has the disadvantage of higher compression set and lower Bashore resilience.

It is an object of the present invention to produce a liquid injection molding organopolysiloxane composition having high hardness and tear strengths without resultant adverse effects on other physical properties, such a composition being particularly suited to the injection molding of large silicone rubber articles.

It is an additional object of the present invention to produce curable liquid injection molding compositions preferably organopolysiloxane compositions that additionally have good shelf stability and good mold release, and may be employed in the manufacture of large silicone rubber articles.

The manufacturing technique of liquid injection molding typically has been liquid injection moldingited to small parts, usually materials weighing less than from about 5 to about 50 grams. Advances in technology are allowing liquid injection molded parts to become larger. Larger parts require larger molds. Larger molds require more time to fill the mold with resin and thus curing must be inhibited for longer times in order to allow the mold to fill before cure may be initiated.

It is an additional object of the present invention to provide novel liquid injection molding inhibitors that will allow the manufacture of larger articles of manufacture than heretofore were possible to be made from curable liquid organopolysiloxane compositions or other curable resins.

It is an additional object of the present invention to provide articles of manufacture manufactured using curable liquid injection molding resins containing the injection molding inhibitors of the present invention or mixtures comprising said injection molding inhibitor compounds wherein said inhibitor compounds cure into the curable resin forming chemical bonds between the injection molding inhibitor compounds of the present invention and the curable resin thereby forming an article of manufacture manufactured from a new composition of matter.

These and other objects will become apparent to those skilled in the art upon consideration of the present specification, examples, and claims.

DETAILED DESCRIPTION OF THE INVENTION

There is provided in the present invention a liquid injection molding organopolysiloxane composition, as a member of a class of moldable and curable resins, combining low viscosity, high strength, good elongation with exceptionally good hardness and tear strength which when combined with a new composition of matter useful as a liquid injection molding inhibitor, which composition of matter is a compound useful for inhibiting premature curing in injection molding compositions having the formula:

$$R_1 O_2C\text{—}CH\text{=}CH\text{—}CO_2R_2$$

wherein $R_1$ may be any suitable organic moiety containing at least two carbon atoms triply bonded one to the other as:

and $R_2$ may be hydrogen, any suitable organic moiety, or $R_1$, said compound allowing larger articles of manufacture to be produced via the techniques of liquid injection molding when the liquid consists essentially of a curable resin, particularly in the case of the present invention a organopolysiloxane. Such a low viscosity organopolysiloxane composition comprises:

(A) 100 parts by weight of an alkenyl, preferably vinyl containing polyorganosiloxane component comprising:
  (1) 70 to 98 parts by weight of a linear high viscosity alkenyl or vinyl end-stopped organopolysiloxane having no more than 25 mole percent of phenyl radicals and having a viscosity of from about 2,000 to about 1,000,000 centipoise at 25° C.,
  (2) 1 to 15 parts by weight of a linear low viscosity organopolysiloxane having at least one terminal alkenyl group per molecule, having an alkenyl or vinyl content that may vary from 0.01 mole percent alkenyl or vinyl to 60 mole percent alkenyl or vinyl, having a viscosity that varies from 50 to about 5,000 centipoise at 25° C. and having no more than 25 mole percent phenyl radicals, and,
  (3) 1 to 15 parts by weight of an alkenyl or vinyl on chain organopolysiloxane having from about 0.1 to about 25 mole percent alkenyl or vinyl, having a viscosity that varies from about 50 to 100,000 centipoise at 25° C. and having no more than about 25 mole percent phenyl radicals;

(B) from about 5 to about 70 parts by weight of a filler;

(C) from about 0.1 to 50 parts per million of the total organopolysiloxane composition of a platinum catalyst;

(D) from about 0.1 to 10 parts by weight a SiH composition selected from the class consisting of hydrogen containing silanes and hydrogen containing organopolysiloxane;

(E) optionally, from about 0.1 to about 6.0 parts by weight a hydroxy containing organopolysiloxane fluid or resin having a viscosity ranging from about 5 to about 100 centipoise at 25° C.; and (F) from about 0.001 to about 1.0 parts by weight per weight of the total liquid injection molding fluid of an injection molding inhibitor compound or compounds, said injection molding inhibitor compound(s) selected from the group consisting of the mono- and di- alkynyl substituted derivatives of maleic acid said compound or compounds having the formula:

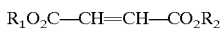

wherein $R_1$ has the formula:

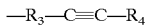

wherein $R_3$ is selected from the group of divalent hydrocarbonradicals consisting of linear or branched alkyl radicals having from 1 to about 10 carbon atoms, linear or branched alkenyl radicals having from 1 to about 10 carbon atoms, linear or branched alkynyl radicals having from 1 to about 10 carbon atoms, cycloalklyl radicals having from 3 to about 12 carbon atoms, cycloalkenyl radicals having from about 3 to 12 carbon atoms, cycloalkynyl radicals having from about 8 to about 16 carbon atoms, fluorinated linear or branched alkyl radicals having from 1 to about 10 carbon atoms, chlorinated linear or branched alkyl radicals having from 1 to about 10 carbon atoms, brominated linear or branched alkyl radicals having from 1 to about 10 carbon atoms, fluorinated linear or branched alkenyl radicals having from 1 to about 10 carbon atoms, chlorinated linear or branched alkenyl radicals having from 1 to about 10 carbon atoms, brominated linear or branched alkenyl radicals having from 1 to about 10 carbon atoms, fluorinated linear or branched alkynyl radicals having from 1 to about 10 carbon atoms, chlorinated linear or branched alkynyl radicals having from 1 to about 10 carbon atoms, brominated linear or branched alkynyl radicals having from 1 to about 10 carbon atoms, hydrocarbonoxy radicals containing at least two carbon atoms, fluorinated hydrocarbonoxy radicals containing at least two carbon atoms, chlorinated hydrocarbonoxy radicals containing at least two carbon atoms, brominated hydrocarbonoxy radicals containing at least two carbon atoms, aryl radicals, linear or branched alkyl aryl radicals, fluorinated aryl radicals, chlorinated aryl radicals, brominated aryl radicals; fluorinated linear or branched alkyl-, alkenyl-, or alkynyl aryl radicals; chlorinated linear or branched alkyl-, alkenyl-, or alkynyl aryl radicals; and brominated linear or branched alkyl-, alkenyl-, or alkynyl aryl radicals; and wherein R4 is selected from the group of monovalent radicals consisting of hydrogen, linear or branched alkyl radicals having from 1 to about 10 carbon atoms, linear or branched alkenyl radicals having from 1 to about 10 carbon atoms, linear or branched alkynyl radicals having from 1 to about 10 carbon atoms, cycloalklyl radicals having from 3 to about 12 carbon atoms, cycloalkenyl radicals having from about 3 to 12 carbon atoms, cycloalkynyl radicals having from about 8 to about 16 carbon atoms, fluorinated linear or branched alkyl radicals having from 1 to about 10 carbon atoms, chlorinated linear or branched alkyl radicals having from 1 to about 10 carbon atoms, brominated linear or branched alkyl radicals having from 1 to about 10 carbon atoms, fluorinated linear or branched alkenyl radicals having from 1 to about 10 carbon atoms, chlorinated linear or branched alkenyl radicals having from 1 to about 10 carbon atoms, brominated linear or branched alkenyl radicals having from 1 to about 10 carbon atoms, fluorinated linear or branched alkynyl radicals having from 1 to about 10 carbon atoms, chlorinated linear or branched alkynyl radicals having from 1 to about 10 carbon atoms, brominated linear or branched alkynyl radicals having from 1 to about 10 carbon atoms, hydrocarbonoxy radicals containing at least two carbon atoms, fluorinated hydrocarbonoxy radicals containing at least two carbon atoms, chlorinated hydrocarbonoxy radicals containing at least two carbon atoms, brominated hydrocarbonoxy radicals containing at least two carbon atoms aryl radicals, linear or branched alkyl aryl radicals, fluorinated aryl radicals, chlorinated aryl radicals, brominated aryl radicals; fluorinated linear or branched alkyl-, alkenyl-, or alkynyl aryl radicals; chlorinated linear or branched alkyl-, alkenyl-, or alkynyl aryl radicals; brominated linear or branched alkyl-, alkenyl-, or alkynyl aryl radicals; and triorganosilyl radicals and wherein $R_2$ may be $R_1$ or selected from the group consisting of hydrogen, triorganosilyl radicals, and siloxanes wherein the structural geometry of the compound around the double bond may be either cis or trans.

This composition may be either cured to an elastomer at room temperature for several hours or may be cured at elevated temperatures, such as, for example, 200° C. for 10 seconds. In one embodiment, the above composition is a two-component composition where the first component, contains at least all of ingredient (C), and the second component, contains all of ingredient (D) and the inhibitor compounds F.

The linear high viscosity alkenyl or vinyl end-stopped organopolysiloxane, A(1), has no more than 25 mole percent of phenyl radicals and a viscosity of from about 2,000 to about 1,000,000 centipoise 25° C., preferably from about 10,000 to about 500,000 at 25° C. These high viscosity organopolysiloxanes may be represented by the general formula:

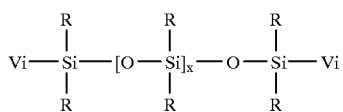
(1)

where Vi stands for alkenyl or vinyl, R is selected from the group consisting of monovalent hydrocarbon radicals and halogenated monovalent hydrocarbon radicals having up to about 20 carbon atoms, and x may vary from about 100 to about 10,000 or even higher, preferably ranging from about 500 to about 2,000. Suitable high viscosity organopolysiloxanes are disclosed in U.S. Pat. No. 3,884,866 hereby incorporated by reference.

The linear low viscosity organopolysiloxane, A(2), has at least one terminal alkenyl or vinyl group per molecule, an alkenyl or vinyl content that may vary from about 0.01 mole percent vinyl to about 60 mole per cent vinyl, preferably from about 0.05 to about 10 mole percent alkenyl or vinyl, a viscosity that varies from about 50 to about 5,000 centipoise at 25° C., preferably from about 50 to 1,000 centipoise at 25° C.; and no more than about 25 mole percent phenyl radicals. These low viscosity organopolysiloxanes may be represented by the general formula:

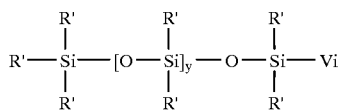
(2)

wherein R' is selected from the group consisting of monovalent hydrocarbon radicals having up to about 20 carbon atoms, halogenated monovalent hydrocarbon radicals having up to about 20 carbon atoms, and alkenyl or vinyl, Vi is alkenyl or vinyl, and y may vary from about 1 to about 750. Suitable low viscosity organopolysiloxanes are disclosed in U.S. Pat. No. 3,884,886 hereby incorporated by reference.

The alkenyl or vinyl on chain organopolysiloxanes, A(3), is important to obtaining the desired properties. Suitable alkenyl or vinyl on chain organopolysiloxanes have from about 0.1 to about 25 mole percent alkenyl or vinyl and preferably from about 0.2 to about 5 mole percent alkenyl or vinyl, a viscosity that varies from about 50 to about 100,000 centipoise at 25° C., preferably from about 100 to about 100,000 centipoise at 25° C., and no more than about 25 mole percent phenyl radicals. These organopolysiloxanes may be characterized as copolymers of (I) siloxane units having the formula:

$$R_a R_b^2 SiO_{(4-a-b/2)} \quad (3)$$

wherein R is selected from the group consisting of monovalent hydrocarbon radicals and halogenated monovalent hydrocarbon radicals having up to about 20 carbon atoms, $R^2$ is an olefinic hydrocarbon radical attached to silicon by a C—Si linkage, and generally contains from 1 to about 20 aliphatic carbons, either straight chain or branched, and preferably from 1 to about 12 carbon atoms linked by multiple bonds, with the stoichiometric subscript a ranging from a value of 0 to about 2 inclusive, and the sum of the toichiometric subscripts a and b ranges from about 0.8 to about 3.0 inclusive, and (II) organopolysiloxane units having the structural formula:

$$R_c SiO_{(4-c)/2} \quad (4)$$

wherein R is selected from the group consisting of monovalent hydrocarbon radicals and halogenated monovalent hydrocarbon radicals having up to about 20 carbon atoms, and the stoichiometric coefficient c ranges in value from about 0.85 to about 2.5, inclusive. $R^2$ may be for example, allyl, methallyl, butenyl, pentenyl, hexenyl, heptenyl, octenyl, ethenyl, and the like, but is preferably vinyl. The copolymer of (I) and (II) generally contains from about 0.5 to 99.5 mole percent of the compound of formula (3) above and from about 0.5 to 99.5 mole percent of the compound of formula (4) above. The preparation of these copolymers is well known in the art, as is taught in U.S. Pat. Nos. 3,436,366 and 3,344,111 hereby incorporated by reference.

Preferred alkenyl or vinyl on chain organopolysiloxanes are linear and have the general formula:

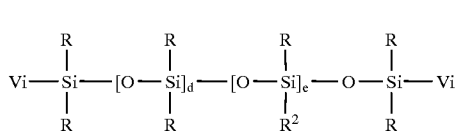
(5)

wherein R is selected from the group consisting of monovalent hydrocarbon radicals and halogenated monovalent hydrocarbon radicals having up to about 20 carbon atoms, $R^2$ is an olefinic hydrocarbon radical attached to silicon by a C—Si linkage, and generally contains from 1 to about 20 aliphatic carbons, either straight chain or branched, and preferably from 1 to about 12 carbon atoms linked by multiple bonds, and d and e are positive integers such that the polymer contains up to approximately 20 mole percent $R^2$. Vi is alkenyl or vinyl. Preferably $R^2$ is vinyl but may also be alkenyl, then the polymer contains from 0.05 to 10 mole percent $R^2$, and the viscosity ranges from about 300 to about 1000 at 25° C.

As previously recited, R is selected from the group consisting of monovalent hydrocarbon radicals and halogenated monovalent hydrocarbon radicals having up to about 20 carbon atoms, that is radicals normally associated as substituent groups for organopolysiloxanes. Thus the radical R may be selected from the class consisting of mononuclear and binuclear aryl radicals such as phenyl, tolyl, xylyl, benzyl, naphthyl, alkylnaphthyl and the like; halogenated mononuclear and binuclear aryl radicals such as chlorophenyl, chloronaphthyl and the like; mononuclear aryl lower alkyl radicals having from 0 to 8 carbon atoms per alkyl groups such as benzyl, phenyl and the like; lower alkyl radicals having from 1 to, 8 carbon atoms such as methyl, ethyl, propyl, butyl, pentyl, hexyl, heptyl, octyl and the like either as straight or branched chain alkyl substituents, lower alkenyl radicals having from 2 to 8 carbon atoms such as vinyl, allyl, and 1-propenyl; halo lower alkyl radicals having from 1 to 8 carbon atoms such as chloropropyl, trifluoropropyl, and cycloalkyl radicals such as cyclobutyl, cyclopentyl and cyclohexyl. Though R may be any of the above, persons skilled in the art will readily recognize that not every R can be a high molecular weight radical and that R should be chosen so as to not adversely affect the vinyl group reactions. Preferably R is a lower alkyl radical of 1 to 8 carbon atoms, such as methyl, ethyl, and phenyl trifluoropropyl. More particularly, R, is at least 70 percent by number methyl.

The SiH composition, (D), serves as a cross linking agent and may be selected from the class consisting of hydrogen containing silanes and hydrogen containing organopolysiloxanes. Hydrogen containing organopolysiloxane can be characterized as copolymers containing at least one unit per molecule having the formula:

$$R_fH_gSiO_{(4-f-h)/2} \tag{6}$$

where the remaining siloxane units in the organopolysiloxane are within the scope of formula (4) above, with the notable exception that the R of formula (4) as well as the R herein should be saturated, f as a value ranging from 0 to about 2, inclusive; and the sum of f and ranges from about 0.8 to about 3.0. The viscosity of the hydrogen ontaining organopolysiloxane should range from about 5 to about 100 centipoise at 25° C.

Included with the hydrogen containing organopolysiloxane described above are MQ resins having units of, for example, $M(R)_2$, $SiO_{1/2}$ and $SiO_2$. Also included therein are MDQ, MTQ, MDT, and MTQ resins with hydrogen substitution. Thus copolymer generally contains from 0.5 to 99.5 mole percent of the units of formula (6) and from 99.5 mole percent of the units of formula (4).

The compounds, oligomers, resins or fluids designated MQ, MDQ, MTQ, MDT, and MT refer to the nomenclature explained in the research monograph by H. A. Liebhafsky, "Silicones Under the Monogram," published by Wiley—Interscience division of John Wiley and Sons, New York (publication date 1978) at pages 99 and. following. In the context of the present invention, substitutional isomerization such as M' being different from M but functioning as an "M" in terms of polymer building blocks as well as D' and D, T and T, and Q' and Q, likewise; there being many varieties of each type of building block, are all encompassed by the simple shorthand notation referred to in the reference and herewith assume the same variability with respect to composition while retaining their respective M, D, T, and Q functionality.

A preferred hydrogen containing organopolysiloxane is a linear organopolysiloxane of the formula:

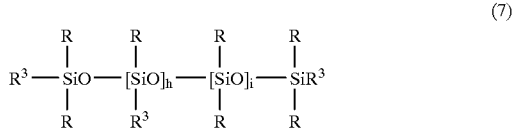

$$(7)$$

wherein R is defined as above, excluding unsaturated compounds, $R^3$ is the same as R excluding unsaturated compounds and with the addition of hydrogen, h varies from 1 to about 1000, and i varies from 5 to about 200. More preferably, h varies from 10 to about 500 and i varies from 5 to about 200.

The hydrogen containing organopolysiloxane, (D), is utilized at a concentration of anywhere from about 0.5 to 25 part by weight per 100 parts by weight (A), and preferably at a concentration of from about 0.5 to about 10 parts by weight per 100 parts by weight (A). It is desirable that in the SiH material there is at least one hydrogen atom for every vinyl group in (A) and preferably from about 1.1 to about 2.5 hydrogen atoms for every vinyl group.

Many types of platinum catalysts for this SiH olefin addition reaction are known and such platinum catalysts may be used for the reaction in the present instance. When optical clarity is required the preferred platinum catalysts are those platinum compound catalysts that are soluble in the reaction mixture. The platinum compound can be selected from those having the formula ($PtCl_2Olefin$) and H($PtCl_3Olefin$) as described in U.S. Pat. No. 3,159,601, hereby incorporated by reference. The olefin shown in the previous two formulas can be almost any type of olefin but is preferably an alkenylene having from 2 to 8 carbon atoms, a cycloalkenylene have from 5 to 7 carbon atoms or styrene. Specific olefins utilizable in the above formulas are ethylene, propylene, the various isomers of butylene, octylene, cyclopentene, cyclohexene, cycloheptene, and the like.

A further platinum containing material usable in the compositions of the present invention is the cyclopropane complex of platinum chloride described in U.S. Pat. No. 3,159,662 hereby incorporated by reference.

Further the platinum containing material can be a complex formed from chloroplatininc acid with up to 2 moles per gram of platinum of a member selected from the class consisting of alcohols, ethers, aldehydes and mixtures of the above as described in U.S. Pat. No. 3,220,972 hereby incorporated by reference.

The catalyst preferred for use with liquid injection molding compositions are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in *Advances in Oroanometallic Chemistry*, volume 17, pages 407 through 447, F. G. A. Stone and R. West editors, published by the Academic Press (New York, 1979). Persons skilled in the art can easily determine an effective amount of platinum catalyst. Generally, an effective amount ranges from about 0.1 to 50 parts per million of the total organopolysiloxane composition.

One example utilized by current technology is the use of platinum compounds that are complexed by highly coordinating ligands such as 2,2'-bipyridyl. Pt bipyridyl exhibits good stability, i.e. there is no curing at low temperatures, however, the curing at high temperatures, e.g. 350° F., is not as fast as might be desirable. Another approach is to premix the platinum and another inhibitor such as 1-ethynyl-1-cyclohexanol. This mixture has a good low temperature stability as well as a good cure rate at 350° F. but has a poor shelf life. When an inhibitor exhibits poor shelf life, the cure rate decreases directly with increasing time of storage.

In order to obtain high tensile strength in the compositions of the present invention, it is desirable to incorporate a filler, (B), into the composition. Examples of the many fillers that may be chosen are titanium dioxide, lithopone, zinc oxide, zirconium silicate, silica aerogel, iron oxide, diatomaceous earth, calcium carbonate, fumed silica, silazane treated silica, precipitated silica, glass fibers, magnesium oxide, chromic oxide, zirconium oxide, aluminum oxide, alpha quartz, calcined clay, asbestos, carbon, graphite, cork, cotton, synthetic fibers, and the like.

The preferred fillers that should be utilized in the composition of the present invention are either a fumed silica or a precipitated silica that has been surface treated. In one method of surface treatment, the fumed silica or precipitated silica is exposed to cyclic organopolysiloxanes under heat and pressure. An additional method of treating fillers is one in which the silica is exposed to siloxanes or silanes in the presence of an amine compound.

A particularly preferred method of surface treating silica fillers employs methyl silane silazane surface treating agents. Methylsilane or silazane surface treated fumed or precipitated silica fillers exhibit the property of flowing easily and also do not increase the low viscosity of the uncured liquid precursor silicone composition. After curing, silazane treated silicas impart an improved tear strength to the cured elastomer. Combining the silazane treatment with composition (A) for in situ treating seems to give the greatest improvement in physical properties. Silazanes treatments are disclosed in U.S. Pat. Nos. 3,635,743 and 3,847, 848 hereby incorporated by reference.

The filler, (B), is generally utilized in a concentration of from about 5 to about 70 parts, preferably 15 to 50 parts filler for each 100 parts by weight of (A). The preferred filler is silazane treated fumed silica or mixtures of silazane treated fumed silica with silazane treated precipitated silica. This latter mixture is particularly preferred containing a weight ratio of fumed silica to precipitated silica of about 25/1 to about 1/1 and preferably from about 10/1 to about 5/1.

Hydroxy containing organopolysiloxane fluid, (E), may be added to extend the shelf life of the liquid injection molding organopolysiloxane composition. Where silazane treated precipitated silica filler is present in the composition, the hydroxy containing organopolysiloxane fluid or resin may be added in conjunction with the precipitated silica filler to obtain extended shelf life and mold release. Suitable hydroxy containing organopolysiloxane fluid has a viscosity of from about 5 to about 100 centipoise at 25° C. and preferably from about 20 to 50 centipoise.

These fluids may be represented by the formula:

$$R_j(OH)_k SiO_{(4-j-k)/2} \quad (8)$$

where R is defined as above, j may range from 0 to about 3, preferably 0.5 to about 2.0, k ranges from 0.005 to about 2, and the sum of j and k ranges from about 0.8 to about 3.0. The hydroxy substitution on the organopolysiloxane fluid or resin is primarily a terminal hydroxy substitution.

To obtain mold release properties employing a combination of silazane treated silica and composition (E), or to obtain extended shelf-life upon the addition of (E) alone, there should be present in composition (B) at least about 2 parts by weight silazane treated silica for each 100 parts by weight of (A) and there should be present as composition (E) from about 1 to about 5 parts by weight for each 100 parts by weight (A).

The ingredients present in composition (C), component 1, may be packaged separately from the ingredients present in composition (D), component II, until the time of cure. Compositions (A), (B), (E), and additives may be divided between either component or wholly added to one component. Premature reactions are avoided in this manner during storage and transport. When it is desired to form the cured silicone rubber composition, the two components are mixed into each other and the composition is allowed to cure. A fairly general practice is to formulate inhibitors such that the cure rates will allow storage of the resin within a liquid injection molding apparatus over short periods of time such as a weekend without the curable composition curing during storage.

Traditionally liquid injection molding systems have two components, a first component that contains a platinum containing catalyst, and a second component that contains a hydride and an inhibitor. The two components are mixed in a static mixer just prior to use in injection molding. Injection molding cavity temperatures are typically 300° F. or more. The primary function of the liquid injection molding inhibitor is to prevent curing of the molding resin until the mold is filled and thereafter, the mold being filled, to allow a rapid cure to ensure short cycle times. The two components may be injected molded directly or dissolved in solvents for application as a film or coating.

In injection molding, the mixing barrel and shot chamber must be cool in order to prevent premature cure. The mold temperature generally varies from about 150° F. to about 500° F. Pigments, thixotropic agents, thermal stabilizers, and the like may be added according to the teachings in the art. It is particularly desirable to add inhibitors in order to obtain a reasonable work life in the catalyzed material. Suitable inhibitors are taught in U.S. Pat. No. 4,256,870 hereby incorporated by reference. One of the most significant problems present in the existing art is the liquid injection moldingitation on article size and weight imposed by the kinetics of the catalyzation and the thermochemistry of the injection molding process. These two parameters presently interact to liquid injection moldingit the size of injection molded silicone rubber articles of manufacture.

U.S. Pat. No. 3,445,420, the teachings of which are hereby incorporated by reference, discloses and claims curable compositions comprising organopolysiloxanes and acetylenic compounds having a boiling point of at least 25° C. where the acetylenic compound has at least one acetylenic moiety contained within the structural framework of the molecule. Although the use of the acetylenic compounds disclosed and claimed in the '420 patent is well-known in the art, practice of the invention represented by the '420 patent and related inventions has not enabled the liquid injection molding of larger molded articles as contrasted with the present invention.

The manner in which the present invention improves upon the prior art is not in the composition of the silicones or other resins used for liquid injection molding but rather resides in the discovery of new compounds that function as inhibitors for the liquid injection molding of silicone fluids and other resins, these new compounds being the acetylenic maleates and fumarates and related derivative novel maleate and fumarate compounds that also function as liquid injection molding inhibitors. The maleates and fumarates are derivative compounds of maleic and fumaric acids which are both four carbon unsaturated dibasic organic acids being related one to the other as the cis and trans isomers of the same four carbon alkene chain, the (Z)but-2-ene-1,4-dioic or cis-but-2-ene-1,4-dioic acid being commonly known in the art as maleic acid and (E)but-2-ene1,4-dioic or trans-but-2-ene-1, 4-dioic acid being commonly known in the art as fumaric acid. Practitioners in the art typically use the common names, i.e. maleic and fumaric acids or maleates and fumarates as salts, esters, and other derivatives; the IUPAC names of the parent acids are specifically recited herein for purposes of antecedence. The alkynyl maleates and fumarates comprising the compounds of the present invention may be half acid half ester or the full ester and may contain more than one carbon carbon double bond and more than one carbon carbon triple bond. Having taught that the compounds of the present invention comprise alkynyl maleates and fumarates and having taught the utility of those same compounds as liquid injection molding inhibitor compounds, the synthesis of analogous compounds by those having ordinary skill in the art of such analogous compounds containing either or both of higher levels of unsaturation whether olefinic or acetylenic, i.e. alkenic or alkynic, and various organic substituents not specifically recited herein can generally be accomplished and those analogous compounds would be expected on the basis of the teachings herein and herewith published to have utility as liquid injection molding inhibitor compounds.

As a new composition of matter enabling the production of larger articles of manufacture via the technique of liquid injection molding using curable silicone fluids or other curable resins, these new compounds impart a novel and enhanced utility to all liquid injection molding compositions where they may be employed as well as to the articles manufactured thereby and therewith. The present invention relieves the limitations of the prior art by enabling the manufacture of injection molded silicone rubber articles that weigh upwards of about 100 g or more.

The novel inhibitor compounds of the present invention are cross-linked or cured into the polymer molecules of the polymerizable or curable resin as a consequence of the process of liquid injection molding and curing of the polymerizable or curable resin. Thus, the cured resins, containing as they do the cross-linked or cured derivative compounds of the new and novel inhibitor compounds of the present invention, are therefor also new and novel compositions of matter. Thus, articles manufactured via liquid injection molding from cured resins containing the cross-linked or cured new and novel inhibitor compounds of the present invention are themselves new and novel by reason of being made from a new and novel composition of matter. These new articles of manufacture may be made larger than heretofore possible by virtue of the improved kinetic stabilization of the liquid injection molding resin compositions or mixtures thereof made possible by the properties of the new and novel compounds of the present invention.

There are several additional embodiments to which the present invention may be directed. For example, mixtures of inhibitors that possess shorter inhibition times than the compounds of the present invention may be formulated to contain the compounds of the present invention as well thereby producing an inhibitor composition possessing an inhibition time intermediate between the inhibition times of the particular component inhibitor compounds. Thus the inhibition times of curable resin mixtures may be more particularly controlled or adjusted depending on the properties of the curable resins being used to produce articles of manufacture using the techniques of liquid injection molding, and the instant technique.

EXAMPLES

The examples hereinafter presented serve to illustrate the utility of these new compositions of matter and instruct those skilled in the art concerning the broad ranges of applicability and utility wherein such new compositions of matter may be employed. By presenting these examples, applicants do not intend to imply any liquid injection moldingitations on the extent of these new contributions to the art by the mere presentation of an illustrative example.

Preparation of Inhibitor Compounds

The following inhibitors were prepared by combining the appropriate precursor alcohol, maleic anhydride, toluene, and a catalytic amount of methane sulfonic acid (MSA) in a flask equipped with a "Dean Stark" trap, magnetic stirrer, and nitrogen atmosphere. The resulting reaction mixtures were heated to reflux until water was no longer observed to be collecting in the "Dean Stark" trap. At that point the reaction mixtures were cooled to room temperature and treated with a solution of sodium bicarbonate and then dried over anhydrous potassium bicarbonate. The volatile components were removed on a Buchi rotary evaporator and the esters then purified by distillation. The compounds were characterized by NMR and gas chromatography. The following maleate esters were prepared:

Example 1

Di(3-butynyl)maleate (DBTYNM). 24 g of 3-butyn-1-ol was reacted with 14 g of maleic anhydride in 35 ml of toluene containing one drop of methane sulfonic acid as catalyst and 100 mg of hydroquinone as stabilizer. Subsequent experiments showed the hydroquinone to not be necessary. (bp=122–125° C./full vacuum, GC purity= 97.4%)[1] H NMR Data: (t, J=1.5 Hz, alkynyl CH), 2.55 (dt, J=6, 1.5 Hz, $CH_2CC$), 4.26 (t, J=6 Hz, $CH_2$—O), and 6.2 (s, maleate olefin CHs).

Di(3-butynyl)maleate (DBTYNM), second preparation, demonstrating reproducibility, 50 g of 3-butyn-1-ol was reacted with 31 g of maleic anhydride in 75 ml of toluene containing one drop of methane sulfonic acid as catalyst (bp=138–142° C./ca. 5 mm Hg) $^1$H NMR data: (t, J=1.5 Hz, alkynyl CH), 2.55 (dt, J=1.5, 6 Hz, $CH_2CC$), 4.26 (t, J=6 Hz, $CH_2$—O), and 6.2 (s, maleate olefin CHs).

Example 2

Dipropargyl maleate (DPM). This material was prepared via the reaction of 20 g of maleic anhydride with 46 g of propargyl alcohol in 325 ml of toluene using 1 drop of methane sulfonic acid. Distillation of the material under vacuum gave 15.4 g of pure product (bp=125–130° C./ca. 4–5 mm Hg, GC purity=98.6%). $^1$H NMR data: 2.58 (m, alkynyl CH), 4.8 (d, J=1.5 Hz, $CH_2$—O), 6.35 (s, maleate olefin CHs).

Example 3

[presence of one drop of methanesulfonic acid. 11.5 g of DPTNM was isolated from] Di(3-pentynyl) maleate (DPTNM). 15 g of 3-pentyn-1-ol was reacted with 8.35 g of maleic anhydride in 25 ml of toluene and in the presence of one drop of methanesulfonic acid. 11.5 g of DPTNM was isolated from the reaction mixture (bp=134–140° C./full vacuum GC purity=98.8%). $^1$H NMR data: 1.77 (t, J=3 Hz, $CH_3$), 2.52 (m, $CH_2CC$), 4.22 (t, J=7 Hz, $CH_2$—O), 6.22 (s, maleate olefin CHs).

Example 4

Mono(3-butynyl)maleate (MBTYNM). The sodium bicarbonate layer from the second preparation of example 1 was carefully acidified with concentrated HCl and then extracted with a mixture of toluene and acetonitrile. After drying over anhydrous sodium sulfate, the solvents were remove under vacuum to yield 8 g of crude mono(3-butynyl) maleate. $^1$H (proton) NMR showed this material to contain approximately 6% DBTYNM, 3% 3-butyn-1-ol, and 7% mono(3-butynyl)fumarate. $^1$H NMR data: 2.02 (t, J=2 Hz, alkynyl CH), 2.58 (dt, J=2, 7 Hz, $CH_2CC$), 4.32 (t, J=7 Hz, $CH_2$—O), 6.36 (s, maleate olefin CHs), and 10.97(broad m, OH). The fumarate olefins were observed at 6.87 ppm, the diester DBTYNM maleate olefins at 6.2, and the 3-butyn-1-ol $CH_2$—O triplet could be observed at ca. 3.75 ppm.

Example 5

Allyl 3-butynyl maleate (ABTNM). 5.0 g of MBTYNM (example 4) was combined with 4.3 g allyl bromide, 30 ml terathydrofuran, 3.5 g potassium carbonate, and 20 mg benzyltriethylammonium chloride. The resulting reaction mixture was heated at reflux for 5.5 hours and then allowed to cool to room temperature where it was stirred overnight. The mixture was then diluted with 50 ml of hexane and filtered to remove solids. The filtrate was washed with an additional 12 ml hexane and then the organics were combined and washed once with saturated sodium bicarbonate solution and twice with water. After drying over anhydrous potassium carbonate the solvents were removed under vacuum to yield 4.8 g of product. NMR analysis showed that in addition to the maleate there was some allyl 3 butynyl fumarate present as well (maleate: fumarate=9:1). $^1$H NMR data: 2.0 (t, J=2 Hz, alkynyl CH), 2.52 (dt, J=2, 7 Hz, CH$_2$CC), 4.28 (t, J=7 Hz, CC—CH$_2$—O), 4.67 (d, J=8 Hz, allyl CH$_2$—O), 5.2–6.2 (m, allylic olefin CHs), and 6.26 (s, maleate olefin CHs). The fumarate olefin peak was observed as a singlet at 6.84.

Example 6

Dipropargyl fumarate (DPF). This material was prepared in a different manner. For this example, 26 g of fumaryl chloride was reacted with 46 g of propargyl alcohol in 200 ml of dichloromethane, in the presence of 37.8 triethyl amine and a small amount of dimethyl aminopyridine. After the reaction was complete, the mixture was filtered and washed with 10% HCl to remove the amines. Concentration under reduced pressure yielded the product as a solid with a melting point of 78–80° C. (purified by subliquid injection moldingation). $^1$H NMR data: 2.52 (t, J=1.5 Hz, alkynyl CH), 4.8 (d, J=1.5 Hz, CH$_2$—O), 6.89 (s, fumarate olefin CHs).

Examples 7 Through 19

Examples 7 through 18 consist of cure evaluation using the Monsanto rheometer. Inhibitor cure performance was evaluated on a Monsanto MDR 2000 rheometer. Such testing is conducted as follows: an uncured liquid injection molding sample is placed in the sample chamber which is maintained at the desired cure temperature. The clamps then close and the top plate starts oscillating. As the material solidifies over time, the torque (S') increases until full cure is achieved. The most important data obtained in these runs for the purposes of illustrating the present invention are as follows:

1) the maximum S' value is related to the physical properties of the cured material;

2) integration of the torque curve allows the determination of cure level vs. time; the times at 2% and 90% of reaction extent (T02 and T90, respectively) are particularly significant as they provide information as to when the cure reaction starts and finishes; and 3) the peak rate value can be used to evaluate the speed or velocity of cure once it begins.

For a liquid injection molding composition to be useful in large part formulation and molding, there should be a significant and observable difference in cure times at 250° F. and 350° F. Cure should be slow at 250° F. to allow for mold filling and very fast at 350° F. in order to accommodate short cycle times.

All of the Monsanto rheometer studies were conducted using a common base formulation that was composed of the following weight fractions:

1) 65 parts of a 40,000 cps vinyl stopped polydimethylsiloxane polymer;

2) 25 parts of a 200 m$^2$/g fumed silica;

3) 4 parts of a 450 cps dimethyl vinyl stopped fluid containing additional vinyl on chain (1.6% vinyl);

4) 4 parts of a 500 cps trimethyl silyl dimethylvinylsilyl terminated polymer, 5) 1 part of a low molecular weight silanol polymer; and 6) 1 part of a silanol functional MQ resin.

Part "A" of the two part liquid injection molding material was prepared by combining 100 parts of the base formulation with 20 ppm Pt as a Pt-divinyl tetramethylsiloxane complex. The part "B" materials were prepared by combining 100 parts of the base formulation with the appropriate amount of inhibitor (see below in examples) and 3.2 parts of a 3:1 blend of an MHQ resin (ca. 1% H as SiH) and a trimethylsilyl chain stopped dimethyl methyl hydrogen polysiloxane polymer (ca. 0.8% H as SiH). Complete liquid injection molding formulations were then prepared by mixing "A" and "B" in a 1:1 weight ratio. In addition to the Monsanto rheometer runs, the test formulations were also cured in compression molded slabs (350° F., 15 minutes) so that physical measurements could also be obtained on sheet materials prepared therefrom. Tensile values were about 1190 psi, tear B values were about 250 ppi, elongations were about 670%, 100% modulus was about 130 and the durometer was about 39.

Included in Table I below are the Monsanto rheometer data for di(3-butynyl)maleate (DBTYNM) based formulations as well as comparative data on other known inhibitors such as diallyl maleate (DAM), 1-ethynyl-1-cyclohexanol (ECH), 2,2'-bipyridyl, and 2-methyl-3-butyn-2-ol (MB). The inhibitor amounts listed refer to the overall concentration in the "A"/"B" blend. Concentrations of the various inhibitors in the base composition used for these comparative evaluations have all been at a constant equimolar level.

TABLE I

Monsanto Rheometer Data for DBTYNM-vs-Controls

| Example Number | Inhibitor (pph) | Cure Temp. (° F.) | S'Max. (lb.-in.) | T02 (sec.) | T90 (sec.) | Peak Rate (lb.-in/min.) |
|---|---|---|---|---|---|---|
| 7a | DBTYNM (0.1) | 250 | 11.69 | 84 | 158 | 19.4 |
| 7b | DBTYNM (0.1) | 350 | 11.24 | 6 | 17 | 97.0 |
| 8a | DBTYNM (0.15) | 250 | 12.7 | 152 | 257 | 15.3 |
| 8b | DBTYNM (0.15) | 350 | 11.6 | 9 | 21 | 84.8 |
| 9a | DAM (0.2) | 250 | 10.67 | 60 | 117 | 24.1 |
| 9b | DAM (0.2) | 350 | 9.91 | 6 | 21 | 69.5 |
| 10a | DAM (0.3) | 250 | 11.25 | 90 | 234 | 14.5 |
| 10b | DAM (0.3) | 350 | 9.27 | 9 | 30 | 57.1 |
| 11a | 2,2'-Bipyridyl (0.2) | 250 | 2.4 | 56 | 598 | 0.4 |
| 11b | 2,2'-Bipyridyl (0.2) | 350 | 3.72 | 10 | 88 | 3.72 |
| 12a | ECH (0.08) | 250 | 10.42 | 8 | 18 | 85.3 |
| 12b | ECH (0.08) | 350 | 10.03 | 4 | 9 | 104.5 |
| 13a | MB (0.06) | 250 | 10.30 | 8 | 25 | 65.5 |
| 13b | MB (0.06) | 350 | 10.29 | 2 | 9 | 109.4 |

As can be seen, DBTYNM provides a superior combination of slow cure at 250° F. as well as a very rapid cure at 350° F. DAM provides a reasonable differentiation between cure rates at the two temperatures, but does not match the results obtained with DBTYNM. Regarding the peak rates at 350° F. for these inhibitors, DBTYNM gave a much higher rate than DAM. ECH and MB, while allowing for a rapid cure at 350° F., did not provide an adequate inhibition at 250° F. Finally, 2,2'-bipyridyl inhibited cure quite well at the lower test temperature but did not allow a rapid cure at the higher test temperature.

Included in Table II. are the Monsanto rheometer data obtained with other alkynyl maleates illustrative of the present invention:

TABLE II

Monsanto Rheometer Data for Other Alkynyl Esters

| Example Number | Inhibitor (pph) | Cure Temp. (° F.) | S'Max. (lb.-in.) | T02 (sec.) | T90 (sec.) | Peak Rate (lb.-in/min.) |
|---|---|---|---|---|---|---|
| 14a | DBF (0.13) | 250 | 9.89 | 16 | 76 | 53.8 |
| 14b | DPF (0.13) | 350 | 10.67 | 4 | 14 | 97.6 |
| 15a | DPM (0.13) | 250 | 11.84 | 65 | 113 | 31.9 |
| 15b | DPM (0.13) | 350 | 11.27 | 6 | 16 | 98.3 |
| 16a | DPTNM (0.17) | 250 | 12.56 | 51 | 79 | 48.7 |
| 16b | DPTNM (0.17) | 350 | 10.07 | 5 | 16 | 86.1 |
| 17a | ABTNM (0.14) | 250 | 10.96 | 63 | 117 | 23.4 |
| 17b | ABTNM (0.14) | 350 | 10.21 | 5 | 16 | 85.8 |
| 18a | MBTYNM (0.1) | 250 | 10.80 | 38 | 69 | 34.7 |
| 18b | MBTYNM (0.1) | 350 | 9.52 | 5 | 15 | 85.5 |

Listed in Table III. is the rheometer data for a formulation based on a blend of DAM and DBTYNM, an inhibitor of the present invention (1:1 molar ratio). This blend was used at 0.14 pph overall concentration.

TABLE III

Monsanto Rheometer Data for a DAM/DBTYNM Blend

| Example Number | Inhibitor (pph) | Cure Temp. (° F.) | S'Max. (lb.-in.) | T02 (sec.) | T90 (sec.) | Peak Rate (lb.-in/min.) |
|---|---|---|---|---|---|---|
| 19a | DAM/ DBTYNM (0.14) | 250 | 11.41 | 104 | 164 | 21.2 |
| 19b | DAM/ DBTYNM (0.14) | 350 | 10.57 | 8 | 21 | 77.5 |

This formulation is intermediate in behavior relative to the result obtained with pure DAM or pure DBTYNM, as compared to data in Table I.

Examples 20 and 21

Liquid injection molding of parts. Two liquid injection molding formulations with base compositions identical to those described in the Monsanto rheometer runs were prepared. Example 20 contained 0.075 pph DBTYNM and Example 21 contained 0.15 pph DAM. The target parts to demonstrate the advantages of the present invention were 75 g computer keypads. The mold was heated to 380° F. and the liquid injection molding composition was injected in 4 seconds and then allowed to cure for 10 seconds for a total clamp time of 14 seconds. The DBTYNM containing formulation, Example 20, produced an excellent part by this procedure. The DAM based formulation was unable to completely fill the mold before curing began, because it cured prematurely, thus an incompletely formed part was manufactured which was unacceptable.

Examples 22 Through 25

FTIR Model studies. Some FTIR (Fourier Transform Infra-Red) model studies were conducted in order to show that the inhibitors of the present invention react into the liquid injection molding formulations upon curing. The formulations used in these experiments were simplified in order to facilitate analysis. The formulations were composed of:

1) 10 parts of a 380 cps vinyl chain stopped fluid;
2) 0.04 parts inhibitor;
3) 0.24 parts of a 35 cps trimethylsilyl stopped methyl hydrogen dimethylpolysiloxane polymer (ca. 1.1% H as SiH); and
4) 75 wppm Pt as a Pt-divinyl tetramethylsiloxane complex.

Thin films of the low viscosity test formulations were spread on KBr salt plates and then FTIR analysis was conducted using a Perkin-Elmer 1600 series FTIR. The peak areas under the SiH peak (ca. 2160 cm$^{-1}$), a small silicone standard peak (ca. 1950 cm$^{-1}$), and the maleate carbonyl peak (ca. 1730 cm$^{-1}$) were measured. The coated KBr salt plates were then placed in a Blue M forced air oven at 225–250° F. for various periods of time. They were then cooled to room temperature and the infrared spectrum via FTIR was then re-determined in order to determine changes in the SiH and carbonyl peaks. This process was repeated until the SiH peak ceased to lose intensity at an appreciable rate, indicating that the cure reaction had become essentially complete.

Example 22

A formulation containing di-allyl maleate was tested first. Nearly 80% of the carbonyl absorbance disappeared before the SiH peak started to diminish. By the time the SiH peak had leveled off due to completion of the hydrosilation reaction, the carbonyl peak due to the inhibitor had essentially disappeared.

Example 23

A formulation containing dibutyl maleate was also studied. This formulation behaved similarly to that in Example 22. The carbonyl peak completely vanished during cure.

Example 24

A formulation containing DBTYNM was studied. Significant carbonyl absorbance was observed even after the cure reaction had nearly gone to completion as evidenced by a leveling off of the disappearance of the SiH peak. This result indicates that even in a severe test where the material is spread out in a thin film and cured in uncovered in a forced air oven that a large amount of the DBTYNM cures in. Therefore, in a liquid injection molding application where the material is sealed in a mold, the DBTYNM inhibitor and related inhibitors would cure into the cured resin as well.

Example 25

The following formulation was evaluated by FTIR as described above:

1) 98 parts of a 225 cps vinyl chain stopped fluid was mixed with
2) 0.45 parts DPTNM;
3) 3 parts of a 35 cps trimethylsilyl stopped methyl hydrogen dimethyl polysiloxane polymer (ca. 1.1% H as SiH); and
4) 2 parts of a 0.5% Pt solution in a 450 cps dimethyl vinyl stopped fluid containing additional vinyl on chain.

At the end of the reaction asjudged by the leveling off of the SiH peak, nearly 80% of the original carbonyl absorbance remained. Therefore, in a liquid injection molding application where the material is sealed in a mold, the DPTNM inhibitor and related inhibitors would cure into the cured resin as well.

Having described the invention, that which is claimed is:

1. A mixture of liquid injection molding inhibitor compounds comprising a compound having the formula:

$$R_1O_2C-CH=CH-CO_2R_2$$

wherein $R_1$ is an organic moiety containing at least two carbon atoms triply bonded one to the other as:

$$-C\equiv C-$$

and $R_2$ is hydrogen, an organic moiety, or $R_1$.

2. The mixture of claim 1 wherein said mixture comprises dipropargyl maleate.

3. The mixture of claim 1 wherein said mixture comprises di(3-pentynyl)maleate.

4. The mixture of claim 1 wherein said mixture comprises mono(3-butynyl)maleate.

5. The mixture of claim 1 wherein said mixture comprises allyl 3-butynyl maleate.

6. The mixture of claim 1 wherein said mixture comprises dipropargyl fumarate.

7. The mixture of claim 1 wherein said mixture comprises di(3-butynyl)maleate.

8. The mixture of claim 4 wherein said mixture additionally comprises an inhibitor compound having an inhibition time shorter than the inhibition time of the compound having the formula:

$$R_1O_2C-CH=CH-CO_2R_2$$

wherein $R_1$ is an organic moiety containing at least two carbon atoms triply bonded one to the other as:

$$-C\equiv C-$$

and $R_2$ is hydrogen, an organic moiety, or $R_1$.

9. The mixture of claim 8 wherein said mixture comprises dipropargyl maleate.

10. The mixture of claim 8 wherein said mixture comprises di(3-pentynyl)maleate.

11. The mixture of claim 8 wherein said mixture comprises mono(3-butynyl)maleate.

12. The mixture of claim 8 wherein said mixture comprises allyl 3-butynyl maleate.

13. The mixture of claim 8 wherein said mixture comprises dipropargyl fumarate.

14. The mixture of claim 8 wherein said mixture comprises di(3-butynyl)maleate.

* * * * *